(12) United States Patent
Chin et al.

(10) Patent No.: US 10,703,707 B2
(45) Date of Patent: Jul. 7, 2020

(54) METHOD FOR PREPARING NITRATE ESTER

(71) Applicant: INDUSTRIAL TECHNOLOGY RESEARCH INSTITUTE, Hsinchu (TW)

(72) Inventors: Chih-Lung Chin, Hsinchu (TW); Shih-Hsien Liu, Jhubei (TW); Wan-Chi Chen, Hsinchu (TW); Kung-Lung Cheng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/413,322

(22) Filed: May 15, 2019

(65) Prior Publication Data
US 2020/0140372 A1    May 7, 2020

Related U.S. Application Data

(60) Provisional application No. 62/756,734, filed on Nov. 7, 2018.

(30) Foreign Application Priority Data

Dec. 28, 2018   (TW) .............................. 107147664 A

(51) Int. Cl.
| C07C 201/02 | (2006.01) |
| B01J 19/00 | (2006.01) |
| C07D 493/04 | (2006.01) |

(52) U.S. Cl.
CPC ......... *C07C 201/02* (2013.01); *B01J 19/0093* (2013.01); *C07D 493/04* (2013.01); *B01J 2219/00862* (2013.01)

(58) Field of Classification Search
CPC .................................................. C07C 201/02
USPC ....................................................... 549/464
See application file for complete search history.

(56) References Cited

U.S. PATENT DOCUMENTS

| 4,552,703 A | 11/1985 | Umemura et al. |
| 4,584,391 A | 4/1986 | Itoh et al. |
| 6,548,693 B2 | 4/2003 | Piccolo et al. |
| 8,536,366 B2 | 9/2013 | Braune et al. |
| 8,558,005 B2 | 10/2013 | Wuellner et al. |
| 2007/0287852 A1 | 12/2007 | Antes et al. |
| 2008/0038175 A1 | 2/2008 | Antes et al. |
| 2010/0137599 A1 | 6/2010 | Hack et al. |

FOREIGN PATENT DOCUMENTS

| CN | 1922127 A | 2/2007 |
| CN | 101001684 A | 7/2007 |
| CN | 101903328 B | 5/2013 |
| CN | 103641840 A | 3/2014 |
| CN | 108610350 A | 10/2018 |
| TW | 200932711 A | 8/2009 |
| WO | WO 2005/077484 A1 | 8/2005 |
| WO | WO 2005/077883 A1 | 8/2005 |
| WO | WO 2009/080755 A1 | 7/2009 |

OTHER PUBLICATIONS

Kuchurov et al., "Sustainable Synthesis of Polynitroesters in the Freon Medium and their in Vitro Evaluation as Potential Nitric Oxide Donors," ACS Sustainable Chem. Eng. 2018, 6, pp. 2535-2540.

Taiwanese Office Action and Search Report, dated Mar. 4, 2020, for Taiwanese Application No. 107147664.

*Primary Examiner* — Taofiq A Solola
(74) *Attorney, Agent, or Firm* — Birch, Stewart, Kolasch & Birch, LLP

(57) ABSTRACT

A method for preparing a nitrate ester is provided. The method includes providing a first solution including a compound (which has at least one hydroxyl group) and a carboxylic acid having 2-5 carbon atoms; providing a second solution including nitric acid, acetic anhydride, and acetic acid; and transferring the first solution and the second solution to a microreactor, obtaining a nitrate ester after a residence time. In particular, the ratio of the weight of nitric acid to the total volume of the acetic anhydride and acetic acid is 1:1 to 1:3.5. The ratio of the molar amount of nitric acid to the hydroxyl group equivalent of the compound is from 1:1 to 15:1.

9 Claims, 2 Drawing Sheets

METHOD FOR PREPARING NITRATE ESTER

CROSS REFERENCE TO RELATED APPLICATIONS

This application claims the benefit of U.S. Provisional Application No. 62/756,734, filed on Nov. 7, 2018, which is hereby incorporated herein by reference.

The application is based on, and claims priority from, Taiwan Application Serial Number 107147664, filed on Dec. 28, 2018, the disclosure of which is hereby incorporated by reference herein in its entirety.

TECHNICAL FIELD

The disclosure relates to a method for preparing nitrate ester.

BACKGROUND

Nitrate esters are important organic compounds and can be widely used in modern science. In the military field, polyol nitrate ester is an important component of an explosive device and a rocket-propelled grenade. Nitrate ester can be used as a cardiotonic drug and vasodilator in medicine. Furthermore, in the field of petroleum processing, nitrate ester with alkyl group can be used as a diesel booster for increasing octane value.

Unfortunately, the preparation of organic nitrate ester (especially nitrate ester with more than one nitryloxy group, like glycerol trinitrate) is connected with safety issues since organic nitrate esters are explosive and therefore difficult to handle even in a diluted solution. In addition to the use of highly corrosive acids, and the need for management of large amounts of aqueous nitrate waste render the difficulty of industrial production of organic nitrates. In addition, even if a batch reactor is used for the preparation of organic nitrate ester, it may cause local overheating and lead to danger due to uneven distribution of reactants.

A persistent aim of the chemical industry is to constantly improve and control chemical reactions. Greater control over reactions may lead to, for example, improvements in safety, increases in reaction product yield and/or purity of highly reactive intermediate products. Therefore, there is a need to develop a novel method for preparing nitrate ester in order to solve the above problems.

SUMMARY

According to embodiments of the disclosure, the disclosure provides a method for preparing nitrate ester. The method includes the following steps: First, a first solution is provided, wherein the first solution consists of a compound and a carboxylic acid having 2-5 carbon atoms. The compound has at least one hydroxyl group. Next, a second solution is provided, wherein the second solution consists of nitric acid, acetic anhydride and acetic acid. Next, the first solution and the second solution are individually transferred to a microreactor to form a mixture, obtaining a nitrate ester after a residence time. In particular, the ratio of the weight of nitric acid to the total volume of the acetic anhydride and acetic acid is 1:1 to 1:3.5. In addition, the ratio of the molar amount of nitric acid in the mixture to the hydroxyl group equivalent of the compound in the mixture is from 1:1 to 15:1 before the residence time (i.e. before the first solution and the second solution undergo a reaction).

A detailed description is given in the following embodiments with reference to the accompanying drawings.

DETAILED DESCRIPTION

The disclosure provides a method for preparing nitrate ester. The method for preparing nitrate ester of the disclosure is a continuous process, such as a continuous process for preparing nitrate ester with a microreactor system.

Since the method for preparing nitrate ester of the disclosure employs a microreactor having microtubes, massive production may be achieved easily and safely by increasing the microtubes of the microreactor. In comparison with a conventional batch reactor, the process of the method for preparing nitrate ester of the disclosure is stable and safe when the nitrification is enlarged, and the reaction time of nitrification can be shortened greatly. In addition, due to the use of specific nitrating agent (having specific components and specific ratio of the components) and the specific ratio of nitrating agent to alcohol compound, the method for preparing nitrate ester of the disclosure can exhibit high yield of nitrate ester and improve purity of nitrate ester.

According to embodiments of the disclosure, the method for preparing nitrate ester of the disclosure includes transferring a solution having a compound with hydroxyl group (such as isosorbide) and a solution having a nitrating agent to a microreactor, obtaining a nitrate ester (such as isosorbide dinitrate (for inhibiting angina pectoris)).

In addition, the method for preparing nitrate ester of the disclosure can be widely used in various nitrification employing alcohol compound (such as glycerin, pentaerythritol, mannitol, trimethylolpropane, or 3-monochloro-1,2-propanodiol) as starting material for preparing nitrate ester (such as glyceryl trinitrate, pentaerythritol tetranitrate, mannitol hexanitrate, propatyl trinitrate, or clonitrate).

Figure 1:
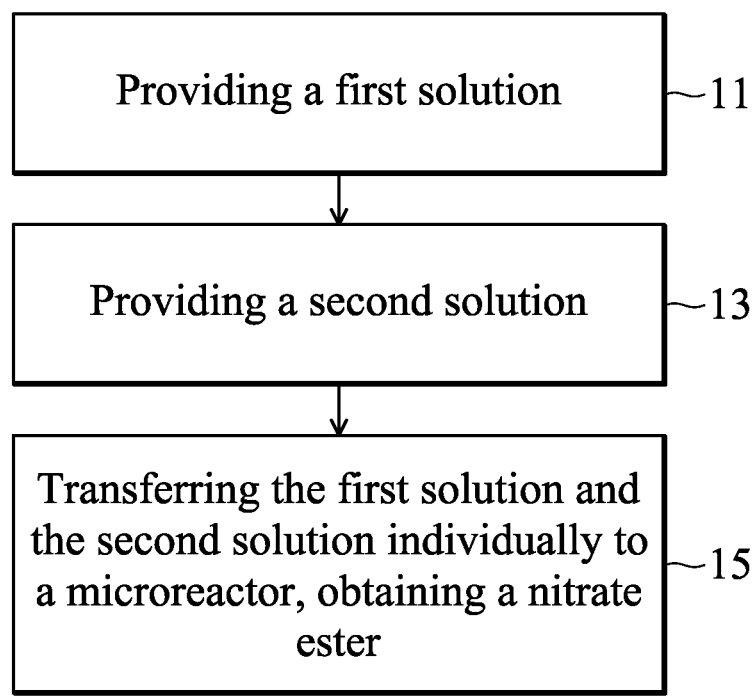
FIG. 1 is a flowchart showing a method for preparing nitrate ester according to an embodiment of the disclosure.

FIG. 1 is a flowchart showing a method for preparing nitrate ester according to an embodiment of the disclosure. The method for preparing nitrate ester of the disclosure includes the following steps: First, a first solution is provided (step 11), wherein the first solution consists of a compound and a carboxylic acid having 2-5 carbon atoms, wherein the compound has at least one hydroxyl group. A second solution is provided (step 13), wherein the second solution consists of nitric acid, acetic anhydride and acetic acid. Next, the first solution and the second solution are individually transferred to a microreactor, obtaining a nitrate ester after reaction (step 15).

According to embodiments of the disclosure, the compound of the first solution is a compound having at least one hydroxyl group. Namely, the compound is an alcohol compound. According to embodiments of the disclosure, the compound of the first solution does not have another functional group which is able to react with nitric acid besides the hydroxyl group. According to embodiments of the disclosure, carboxylic acid having 2-5 carbon atoms can be a carboxylic acid having two carbon atoms, a carboxylic acid having three carbon atoms, a carboxylic acid having four carbon atoms, or a carboxylic acid having five carbon atoms.

For example, carboxylic acid having 2-5 carbon atoms can be acetic acid, propionic acid, butyric acid, or pentanoic acid.

According to embodiments of the disclosure, in the first solution, the ratio of the volume of carboxylic acid having 2-5 carbon atoms to the weight of the compound can be from 1 mL/g to 10 mL/g, such as 2 mL/g, 3 mL/g, 4 mL/g, 5 mL/g, 6 mL/g, 7 mL/g, 8 mL/g, or 9 mL/g.

According to embodiments of the disclosure, the nitric acid of the second solution has a concentration not less than 98%, such as from about 98% to 100%. Namely, the higher the concentration of the nitric acid is, better results. Since it is inevitable that nitric acid will absorb moisture in practical use, the second solution of the disclosure employs nitric acid with a concentration not less than 98%. Since the second solution consists of nitric acid, acetic anhydride and acetic acid, the second solution does not substantially include water (i.e. without intentional addition of water into the second solution). According to embodiments of the disclosure, when nitric acid of the second solution has a concentration less than 98% or the second solution substantially includes water (i.e. water is intentionally added into the second solution), it would result in poor yield and purity of the obtained nitrate ester.

According to embodiments of the disclosure, the volume ratio of acetic anhydride to acetic acid is from 3:1 to 1:3, such as about 2:1, 1:1, or 1:2. According to embodiments of the disclosure, the ratio of the weight of nitric acid to the total volume of the acetic anhydride and acetic acid is 1:1 to 1:3.5, such as about 1:1.5, 1:2, 1:2.5, or 1:3. When the ratio of the weight of nitric acid to the total volume of the acetic anhydride and acetic acid is too low or too high, it would result in poor yield and purity of the obtained nitrate ester.

According to embodiments of the disclosure, the second solution of the disclosure serves as nitrating agent to react with the compound having hydroxyl group to undergo a nitrification, obtaining the nitrate ester. According to embodiments of the disclosure, the second solution of the disclosure is free of sulfuric acid, in order to avoid reducing the purity of the obtained nitrate ester. In addition, according to embodiments of the disclosure, the second solution of the disclosure is free of chlorine-containing compound (such as dichloromethane). When the second solution includes dichloromethane, the gasification of dichloromethane may occur since dichloromethane has a low boiling point and the reaction (combining the first solution and the second solution) is exothermic. According to embodiments of the disclosure, since the nitrating agent of the method for preparing nitrate ester of the disclosure consists of nitric acid, acetic anhydride and acetic acid, the nitric acid could be used repeatedly after simple treatment.

According to embodiments of the disclosure, in the mixture (i.e. initial mixture) of the first solution and the second solution in the microreactor, the ratio of the molar amount of nitric acid to the hydroxyl group equivalent of the compound is from 1:1 to 15:1. Namely, before the first solution reacts with the second solution, the ratio of the molar amount of nitric acid in the mixture to the hydroxyl group equivalent of the compound in the mixture is from 1:1 to 15:1. According to embodiments of the disclosure, the ratio of the molar amount of nitric acid to the hydroxyl group equivalent of the compound can be 3:1, 4:1, 5:1, 6:1, 7:1, 8:1, 9:1, 10:1, 11:1, 12:1, 13:1, or 14:1. When the ratio of the molar amount of nitric acid to the hydroxyl group equivalent of the compound is too low, the nitrification would be incomplete resulting in reducing the yield of the nitrate ester. When the ratio of the molar amount of nitric acid to the hydroxyl group equivalent of the compound is too high, nitric acid would be excess and thus more alkaline water solution should be added to neutralize nitric acid, resulting in increasing cost.

Figure 2:
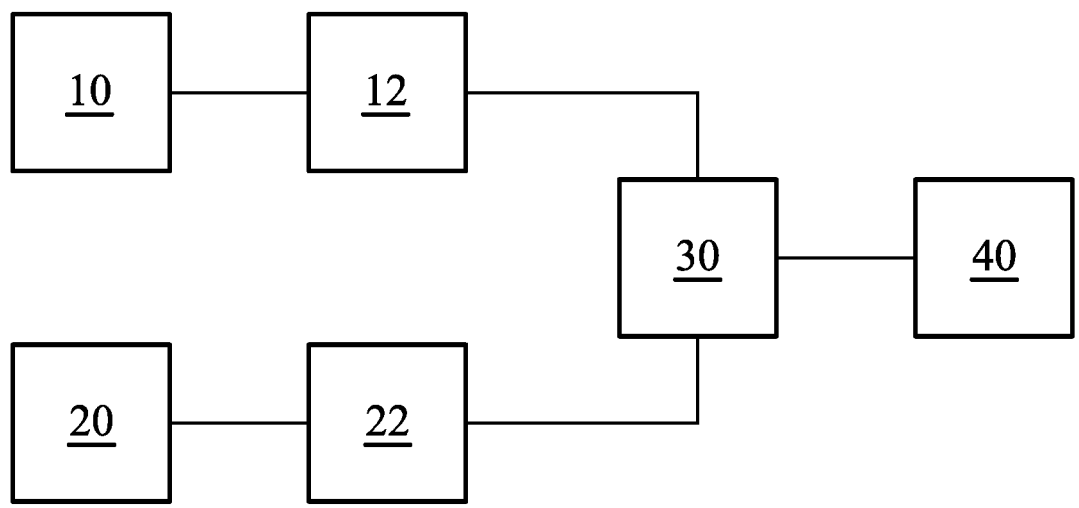
FIG. 2 is a schematic view of a microreactor system for preparing nitrate ester according to an embodiment of the disclosure.

FIG. 2 is a schematic view of a microreactor system 100 for preparing nitrate ester according to an embodiment of the disclosure. Herein, the first solution of the disclosure is disposed in a first tank 10 of the microreactor system 100, and the second solution of the disclosure is disposed in a second tank 20 of the microreactor system 100. The first tank 10 and the second tank 20 have a control element individually in order to transfer the first solution in the first tank 10 via a first channel 12 into a microreactor 30 at a first flow rate and transfer the second solution in the second tank 20 via a second channel 22 into a microreactor 30 at a second flow rate.

When the first solution and the second solution are transferred into the microreactor 30 to form a mixture and then the mixture undergoes a reaction in the microreactor 30 for a residence time (such as from 30 s to 200 s), nitrate ester can be collected via a collector 40. According to embodiments of the disclosure, the microreactor 30 has at least one set of microtube, wherein the inner diameter of the microtube can be from 0.05 mm to 2 mm, such as about 0.1 mm, 0.5 mm, 0.8 mm, 1 mm, or 1.5 mm. According to embodiments of the disclosure, the first flow rate of the first solution in the first channel 12 is from about 0.05 mL/min to 1.5 mL/min, and the second flow rate of the second solution in the second channel 22 is from about 0.05 mL/min to 1.5 mL/min. According to embodiments of the disclosure, the microreactor can be set at a temperature between 0° C. to 30° C. when the mixture goes through the microreactor.

According to embodiments of the disclosure, in the microreactor 30, the ratio of the molar amount of nitric acid to the hydroxyl group equivalent of the compound can be controlled by adjusting the first flow rate and the second flow rate. According to embodiments of the disclosure, due to the high thermal exchange efficiency of the microtube of the microreactor, the problem of local overheating will not be generated during the nitrification, thereby enhancing safety and stability of the process. In addition, since the mixture undergoes reaction and continuously flows in the microreactor, the residence time (i.e. reaction time) of the nitrification can be precisely controlled by adjusting the length of the microtube of the microreactor and/or the flow rate of the first and second solutions.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

Isosorbide (25.04 mmol) (having a structure of

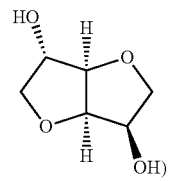

and acetic acid (acetic acid, 20 mL) were mixed to form a first solution (the ratio of the volume of acetic acid to the weight of isosorbide is 5.46:1), and then the first solution was disposed in a first tank. Next, nitric acid (with a concentration of 98%, 10 mL) (234.85 mmol), acetic anhydride (25 ml), and acetic acid (acetic acid, 15 ml) were mixed to form a second solution (the ratio of the weight of nitric acid to the total volume of acetic anhydride and acetic acid is 1:2.7, and the volume ratio of acetic anhydride to acetic acid is 5:3), and then the second solution was disposed in second tank. Next, the first solution in the first tank was transported via a channel to a microreactor at a flow rate of 0.2 mL/min, and the second solution in the second tank was transported via a channel to a microreactor at a flow rate of 0.5 mL/min. When the first solution was mixed initially with the second solution in the microreactor, the ratio of the molar amount of nitric acid to the hydroxyl group equivalent of isosorbide was about 5:1. The first solution reacted with the second solution in the microtube of the microreactor (the temperature of the microreactor was controlled at about 20° C.), wherein the microtubes of the microreactor have a length of 105 cm, the material of the microtubes in the microreactor was PTFE (polytetrafluoroethylene) with an inner diameter of about 1 mm. The residence time (reaction time) of the first solution and the second solution in the microtube of the microreactor was about 70 seconds, and the end of the microtube was connected to a collector, and water was disposed in the collector. After reacting, the result was introduced into the collector (at a temperature of about 0° C.). A white solid precipitate was observed in ice water. After filtering and drying, isosorbide dinitrate was obtained. The purity and yield of isosorbide dinitrate was determined by gas chromatography and the result is shown in Table 1. The results of nuclear magnetic resonance spectrometry of isosorbide dinitrate of Example 1 are shown below. $^1$H NMR (CDCl$_3$, 400 MHz): δ5.42-5.39 (m, 2H), 5.05-5.01 (m, 1H), 4.62-4.59 (m, 1H), 4.20-4.10 (m, 3H), 3.99-3.94 (m, 1H).

Comparative Example 1

Comparative Example 1 was performed in the same manner as in Example 1 except that the flow rate of the second solution was reduced from 0.5 mL/min to 0.06 mL/min. As a result, when the first solution was mixed initially with the second solution in the microreactor, the ratio of the molar amount of nitric acid to the hydroxyl group equivalent of isosorbide was about 0.6:1. Table 1 shows the yield and purity of isosorbide dinitrate prepared by Comparative Example 1.

Comparative Example 2

Comparative Example 2 was performed in the same manner as in Example 1 except that nitric acid with a concentration of 65% substitutes for nitric acid with a concentration of 98%. Table 1 shows the yield and purity of isosorbide dinitrate prepared by Comparative Example 2.

Comparative Example 3

Comparative Example 3 was performed in the same manner as in Example 1 except that nitric acid with a concentration of 80% substitutes for nitric acid with a concentration of 98%. Table 1 shows the yield and purity of isosorbide dinitrate prepared by Comparative Example 3.

Example 2

Example 2 was performed in the same manner as in Example 1 except that the flow rate of the second solution was reduced from 0.5 mL/min to 0.25 mL/min. As a result, when the first solution was mixed initially with the second solution in the microreactor, the ratio of the molar amount of nitric acid to the hydroxyl group equivalent of isosorbide was about 2.5:1. Table 1 shows the yield and purity of isosorbide dinitrate prepared by Example 2.

TABLE 1

| | Flow rate | | | the ratio of the molar amount of nitric acid in the mixture to the hydroxyl | | |
|---|---|---|---|---|---|---|
| | first solution | second solution | nitric acid concentration | group equivalent of isosorbide | purity | yield |
| Example 1 | 0.2 mL/min | 0.5 mL/min | 98% | ~5 | 98% | 92% |
| Comparative Example 1 | 0.2 mL/min | 0.06 mL/min | 98% | ~0.6 | 85% | 58% |
| Comparative Example 2 | 0.2 mL/min | 0.55 mL/min | 65% | ~5 | 40% | 85% |
| Comparative Example 3 | 0.2 mL/min | 0.52 mL/min | 80% | ~5 | 65% | 88% |
| Example 2 | 0.2 mL/min | 0.25 mL/min | 98% | ~2.5 | 88% | 80% |

As shown in Table 1, when the ratio of the molar amount of nitric acid in the mixture to the hydroxyl group equivalent of isosorbide is too low or the concentration of nitric acid was less than 98%, the yield or purity of the product (isosorbide dinitrate) was significantly decreased (as Comparative Examples 1-3). To the contrary, when the ratio of the molar amount of nitric acid in the mixture to the hydroxyl group equivalent of isosorbide is from 2:1 to 15:1 or the concentration of nitric acid was not less than 98%, the yield of the product (isosorbide dinitrate) prepared by Examples 1-2 was greater than or equal to 80% and the purity of the product (isosorbide dinitrate) prepared by Examples 1-2 was greater than or equal to 88%.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A method for preparing nitrate ester, comprising:
   providing a first solution, wherein the first solution consists of a compound and a carboxylic acid having 2-5 carbon atoms, wherein the compound is isosorbide, glycerin, pentaerythritol, mannitol, trimethylolpropane, or 3-monochloro-1,2-propanodiol, and wherein the carboxylic acid having 2-5 carbon atoms is acetic acid, propionic acid, butyric acid, or pentanoic acid;

providing a second solution, wherein the second solution consists of nitric acid, acetic anhydride and acetic acid, wherein the ratio of the weight of nitric acid to the total volume of the acetic anhydride and acetic acid is 1:1 to 1:3.5;

transferring the first solution and the second solution to a microreactor to form a mixture, and obtaining a nitrate ester after a residence time, wherein the ratio of the molar amount of nitric acid in the mixture to the hydroxyl group equivalent of the compound in the mixture is from 1:1 to 15:1, and wherein the nitrate ester is isosorbide dinitrate, glyceryl trinitrate, pentaerythritol tetranitrate, mannitol hexanitrate, propatyl trinitrate, or clonitrate.

2. The method for preparing nitrate ester as claimed in claim 1, wherein nitric acid has a concentration not less than 98%.

3. The method for preparing nitrate ester as claimed in claim 1, wherein the residence time is from 30 s to 200 s.

4. The method for preparing nitrate ester as claimed in claim 1, wherein the flow rate for transferring the first solution to the microreactor is from 0.05 mL/min to 1.5 mL/min.

5. The method for preparing nitrate ester as claimed in claim 1, wherein the flow rate for transferring the second solution to the microreactor is from 0.05 mL/min to 1.5 mL/min.

6. The method for preparing nitrate ester as claimed in claim 1, wherein the volume ratio of acetic anhydride to acetic acid is from 3:1 to 1:3.

7. The method for preparing nitrate ester as claimed in claim 1, wherein the microreactor has a microtube with an inner diameter from 0.05 mm to 2 mm.

8. The method for preparing nitrate ester as claimed in claim 1, wherein the ratio of the volume of the carboxylic acid having 2-5 carbon atoms to the weight of the compound is from 1 mL/g to 10 mL/g.

9. The method for preparing nitrate ester as claimed in claim 1, wherein the flow rate for transferring the second solution to the microreactor is 0.25 mL/min to 0.5 mL/min.

* * * * *